United States Patent [19]
Brownstein et al.

[11] 4,012,423
[45] Mar. 15, 1977

[54] PROCESS FOR THE PRODUCTION OF EPOXIDES
[75] Inventors: Arthur M. Brownstein, Wyckoff; John A. Jung, Somerset; Robert Hansen, Belleville, all of N.J.
[73] Assignee: Chem Systems, Inc., New York, N.Y.
[22] Filed: July 18, 1975
[21] Appl. No.: 597,037

Related U.S. Application Data
[63] Continuation of Ser. No. 444,836, Feb. 22, 1974, abandoned, which is a continuation-in-part of Ser. No. 348,970, April 9, 1973, abandoned.
[52] U.S. Cl. .......................................... 260/348 R

[51] Int. Cl.$^2$ ...................................... C07D 301/02
[58] Field of Search ............................... 260/348 R Primary Examiner—Norma S. Milestone
Attorney, Agent, or Firm—Bert J. Lewen

[57] ABSTRACT

Epoxy compounds are produced by the vapor phase deacyloxylation of vicinal hydroxyesters in the presence of a basic material. The co-product carboxylic acid may be reacted with olefins to form additional hydroxyesters.

16 Claims, No Drawings

PROCESS FOR THE PRODUCTION OF EPOXIDES

RELATED APPLICATIONS

This application is a continuation of application Ser. No. 444,836, filed Feb. 22, 1974 and now abandoned which, in turn, is a continuation-in-part of U.S. application Ser. No. 348,970, filed Apr. 9, 1973 and now abandoned.

DESCRIPTION OF THE INVENTION

This invention relates to a process for production of oxiranes. More particularly, this invention relates to a vapor phase process for the synthesis of oxiranes from vicinal hydroxyester in the presence of a basic material.

Oxiranes, such as ethylene oxide, propylene oxide, and butylene oxide, are useful intermediates in the manufacture of diols and polyols. These di- and polyhydric alcohols, in turn, enjoy widespread use as coolants and in the manufacture of polyethers and polyester resins. Oxiranes are also used for the preparation of basic polyethers, high molecular weight polyols, and block polymers, e.g., poly(ethylene-propylene) adduct of pentaerythritol.

Oxiranes are conventionally produced by vapor phase or liquid phase oxidation of the corresponding olefins. The vapor phase technology is suitable only for ethylene oxide synthesis and, even in this instance, the selectivities are not as great as desired, much of the olefins being converted to $CO_2$ and $H_2O$.

Higher olefins cannot be converted to epoxides by vapor phase oxidation, since allylic attack and olefin oxidation become the major reactions. Thus, higher epoxides are made in the liquid phase by oxidation with alkyl hydroperoxides or peracids. These techniques result in by-products, such as alcohols, olefins or acids, whose recovery and sale are essential for economical epoxide manufacture. An alternate technique for higher epoxide synthesis is via hypochlorous acid addition to the olefin followed by alkaline hydrolysis. Once again, a by-product is obtained, i.e., NaCl or $CaCl_2$, whose economical sale is necessary for the process to be competitive.

In accordance with the invention, it has been discovered that epoxides can be obtained in good yields and with minimum by-product production by the vapor phase deacyloxylation of vicinal hydroxyesters in the presence of a basic material. The deacyloxylation produces the corresponding oxirane and an equimolar amount of the carboxylic acid as shown in the following equation:

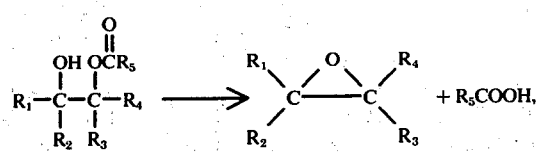

wherein $R_1$, $R_2$, $R_3$, $R_4$ and $R_5$ may be hydrogen; alkyl, alkenyl or alkynyl up to 16 carbon atoms; an aryl group, such as phenyl or naphthyl; cyano;

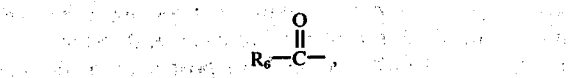

where $R_6$ is hydrogen, alkyl, alkoxy, carbomethoxy, or carboacyl. The aforesaid hydrocarbon groups may be substituted with electron-withdrawing groups, e.g., one or more halo, nitro, sulfo or cyano groups. Additionally, the aryl group may be substituted with alkyl groups having 1 to 4 carbon atoms; and the alkyl groups, with a phenyl group. Preferably, at least two of the aforesaid R groups are hydrogen, and the remaining ones hydrogen, methyl, ethyl, propyl, butyl, or phenyl. $R_1$ and $R_4$ may be joined as common members of a cyclic compound having from 4 to 16 carbon atoms, such as cyclobutane, cyclohexane and cyclododecane. $R_5$ is preferably alkyl having from 1 to 3 carbon atoms with or without electron-withdrawing groups.

Examples of suitable hydrocarbon radicals substituted with electron-withdrawing groups are: trichloromethyl, tribromomethyl, trifluoromethyl, chlorodifluoromethyl, fluorodichloromethyl, bromodichloromethyl, bromodifluoromethyl, cyanomethyl, dichloroethyl, nitromethyl, iodomethyl, sulfomethyl, difluoropropyl, nitrophenyl, fluorophenyl, 2,4-difluorophenyl, 2,4-dibromophenyl, 2,4,6-trichlorophenyl, p-chlorophenyl, p-bromophenyl, p-sulfophenyl, p- and m-cyanophenyl, iodophenyl, chloro- and fluoronaphthyl, dinitronaphthyl, chloro- and bromocyclohexyl, chloronorbornyl and bromodecalin. $R_1$ and $R_5$ may also be acetyl, carboxyl, carbomethoxy, carboethoxy, aldehydic and carboacetyl. Vinylogous acid and ester groups may be employed, as for example the maleic acid half-ester of isopropanol.

The process is markedly superior to the deacyloxylation in aqueous sodium hydroxide solution described in U.S. Pat. No. 3,453,189 and the pyrolysis of hydroxyacetates taught in U.S. Pat. No. 2,415,378. In the first case, the base immediately reacts with the propylene oxide formed to yield propylene glycol and the salt of the carboxylic acid. In the second patent, the pyrolysis yields allyl alcohol, rather than the oxirane compound.

Illustrative examples of the hydroxyesters suitable as starting material in this invention are those derived from such olefins as ethylene, propylene, butylenes, pentenes, styrene and alpha-methylstyrene. Also suitable are substituted olefins such as allyl alcohol and allyl chlorides. Moreover, non-conjugated diolefins, such as 1,4-hexadiene, are suitable for this invention. In this instance, the product would be the corresponding diepoxide, whereas with such substituted olefins as allyl chloride, the product would be epichlorohydrin.

The ester is most preferably of acetic acid because of its ready availability. Other acids which may be used include propionic acid, butyric acid, benzoic acid, chloroacetic acid, trichloroacetic and phenylacetic acid.

The oxirane compounds which can be prepared by practicing the instant invention include: ethylene oxide; propylene oxide; 2,3-dimethyloxirane; 2,2-dimethyloxirane; phenyloxirane; 2-methyl-2-phenyloxirane; 2-n-butyloxirane; cyclohexene oxide; cyclopentene oxide; stilbene oxide; cyclododecene oxide; cyclooctene oxide; 2-cyclohexyloxirane; norbornene oxide; n- and isodecyloxirane; n- and isoheptyloxirane; and n- and isohexadecyloxirane.

It is essential in the practice of the invention to have a basic material present in the reaction zone. In copending U.S. application Ser. No. 348,940, it is said that the basic material is a catalyst which is non-volatile and does not decompose. Without being bound to a particular theory, it has now been discovered that the basic material, in fact, rather than being truly catalytic, reacts with the hydroxycarboxylate stoichiometrically. Using, for example, sodium acetate as the basic material in a reaction for forming propylene oxide from propylene hydroxyacetate, the acetate portion of the basic material first reacts with the hydrogen on the hydroxyl group of the hydroxyacetate, thereby activating the remaining oxygen atom. The activated oxygen attaches to the acetate carbon forming the propylene oxide and splitting off a mole of acetate ion. The acetate ion thus generated reacts with the sodium ion and provides additional sodium acetate which in turn reacts with another mole of the feed. Thus, it can be seen that the basic material in the reaction zone is in dynamic mobile equilibrium: it is continually regenerated. This equilibrium enables the process to be performed with a small amount of the basic material, thus giving the basic material the appearance of functioning catalytically.

In the production of propylene oxide as described in Example 9, the carbonate portion of the sodium carbonate originally charged to the reaction zone reacts with the feed to form carbonic acid which volatilizes and leaves the reaction zone. The sodium ion reacts with the acetic acid coproduct to form sodium acetate. This latter compound, thereafter, serves as the basic material and reacts stoichiometrically with additional hydroxyester. This "in situ" formation of sodium acetate is fundamentally no different from the process wherein the sodium acetate is added to the reaction zone at the outset. Once produced, the sodium acetate is continually replaced by fresh sodium acetate arising from the acetate moiety of the hydroxyester charged to the reactor. The acetate portion of the sodium acetate is continually removed from the reactor as acetic acid. Whether dynamic mobile equilibrium actually takes place may depend upon the reaction conditions. It may be envisioned that certain basic materials may be added which maintain the reaction without the formation of the carboxylate.

It has generally been found that the preferred basic materials have a pH of from about 8 to 13 in a 0.1 molar aqueous solution. Materials having a lower basicity are inadequate to react with the hydroxyesters. Without intending to limit the invention to any particular mechanism, it is believed that so long as the reaction is performed in a basic environment, it will proceed satisfactorily to form the oxirane product.

In view of the foregoing, it will be readily understood that the most preferred basic materials of the invention are alkaline carboxylates, wherein the carboxylate corresponds to the carboxylic acid co-product formed in the reaction. The group I, II and IIIA basic metal carboxylates are most preferred, particularly sodium, potassium, lithium, calcium and barium. However, with the understanding that the following materials may be converted to the carboxylates in situ, the following additional materials may be used: the Group I, II and IIIA basic metal simple oxides and complex oxides and organic bases. (Simple and complex oxides are discussed in Sanderson, "Chemical Periodicity," Reinhold Publ. Co. (1960).) In order of decreasing preferance, borates, phosphates, oxides and carbonates may be employed. Other materials are the alkali and alkaline earth metal salts of boric acid, e.g., sodium borate, potassium metaborate, calcium metaborate, sodium aluminate and sodium silicate.

Still other materials which may be used include magnesium carbonate, barium oxide, zinc oxide, nickel oxide, and sodium pyrophosphate. The organic bases, which generally would be absorbed on a support, include the aromatic nitrogen compounds, e.g., pyridine, quinoline and acridine, and high molecular weight alkylamines having a boiling point in excess of 220° C. More volatile materials may be advantageously used by being chemisorbed on a non-volatile material. These materials may be used alone or in combination with other materials.

The basic materials, both inorganic and organic, can be unsupported or supported on such neutral or basic carriers as alpha-alumina, silicon carbide, zirconium silicate and aluminum silicate. Acid supports are not desirable since they favor the formation of alcehydes.

The hydroxyesters may be fed to the reaction zone alone or, if desired, diluted with a carrier gas. The carrier gas acts as a heat sink and also serves to lower the partial pressure of the hydroxyester in the reaction. The carrier gas may be a liquid, i.e., condensable at room temperature, such as benzene, toluene, xylenes, pseudocumene and water. Non-condensable carrier gases may also be used. These include nitrogen, helium, and carbon dioxide. Generally, where a carrier is used, the hydroxyesters are from about 10 to about 75% by weight, preferably from 25 to 60% of the total feed.

The temperature of the reaction must be sufficient to maintain the hydroxyester in the vapor phase under reaction conditions. Suitable temperature ranges vary depending on the particular hydroxyester, the presence of a carrier gas and the system pressure. Generally, deacyloxylation of the hydroxyacetate proceeds at a temperature of from about 250° C. to about 600° C., preferably from 250° to 450° C. and most desirably 350° to 425° C.

A wide range of pressures may be used, including high pressures up to 400 psia and vacuum down to 0.1 psia. Of key importance is the partial pressure of the hydroxycarboxylate. Generally, partial pressures over 100 psia are not used, and, for ease of operation, atmospheric pressure is often preferred. However, surprisingly, it has been found that reduced pressure operation results in higher conversations without loss of selectivity. More specifically, therefore, it is preferred that the partial pressure be from 1 to 15 psia, most desirably from 2 to 8 psia.

The contact time (calculated on an empty tube basis) of the hydroxyester within the reactor is from about 0.001 to 20 seconds, preferably from 0.2 to 5 seconds and most desirably from 0.5 to 5 seconds.

In the dynamic mobile equilibrium process, for optimum conversions, feed rates of from 0.5 to 1000 moles of the hydroxycarboxylate per mole of basic material per hour are used. More preferably, the feed rate is from 5 to 250 moles/mole/hour and most desirably from 10 to 100 moles/mole/hour.

Where the basic material is maintained in a molten state, such as shown in Example 14 below, it is not necessary to observe the foregoing limits on feed rates, since an excess of the basic material is not detrimental.

Also, the reaction of the invention may be performed without the need of the continued regeneration of the basic material as described above. For example, stoichiometric amounts of the basic material may be used. Specifically, one mole of powdered sodium carbonate and one mole of propylene hydroxyacetate vapor may be reacted to form one mole of propylene oxide and one mole of sodium acetate. Both of these reaction products are removed from the reaction zone and processed to recover the propylene oxide.

The optimum combination of temperature, contact time, carrier gas concentration, and other reaction conditions can be readily determined by those skilled in the art by a limited series of screening runs.

The gas exiting from the reactor may be conveniently quenched in cooling coils or in a cold trap maintained at a temperature from about −80° to 25° C. The oxirane can be separated from the carboxylic acid and condensed carrier, if used, by distillation. Prior to separation, the oxiranes may be readily identifiable in the reaction mixture by gas chromatography.

In a preferred embodiment of the invention, the carboxylic acid co-product obtained in the course of the reaction is recycled and reacted with a precursor olefin to produce additional hydroxyesters. As an example of this procedure, the olefin is dissolved in the carboxylic acid and contacted with a catalyst such as palladium diacetate and sodium nitrate at 80° C. (This process is described in British Pat. No. 1,124,862, the disclosure of which is incorporated by reference herein.) The hydroxyester formed is then used to form additional oxirane compounds in accordance with the teaching of this invention. By following this preferred embodiment, oxiranes are produced directly from olefins without the need for any substantial by-product disposal.

The invention is further described by the following illustrative examples, wherein conversion is defined as the number of moles of hydroxyester undergoing deacyloxylation and does not include that amount undergoing disproportionation to diacetate and diol. Selectivity to propylene oxide, propionaldehyde, acetone and allyl alcohol is defined as the number of moles of each of these materials produced divided by the total moles of reacted hydroxyester deacyloxylated. The hydroxyester which is disproportionated to the corresponding diol and diacetate is reported separately. The bulk of these materials can be recycled or hydrolysed to the corresponding glycols. All the runs are performed at atmospheric pressure.

EXAMPLE 1

In Run No. A, an isomeric mixture of the vicinal hydroxyacetates of propylene and an equal weight of solvent m-xylene is fed into a ½ × 13 stainless steel tube packed with 1.8g sodium borate ($Na_2B_4O_7$) at a rate of 60 ml./hour (contact time equivalent to 1 second) and placed in a furnace. The temperature of the tube is maintained at 385° C. and the pressure is atmospheric. Exit gases are quenched by a cooling coil maintained at 25° C. and a cold trap at −35° C. In a comparative example, Run No. B, the reaction temperature is maintained at 450° C. and no basic material is used. The results of the two runs are shown in the following table:

TABLE I

|  | Run No. A - Basic Material $Na_2B_4O_7$ | Run No. B Open Tube |
|---|---|---|
| Conversion, % | 18.5 | 13.0 |
| Selectivity, % |  |  |
| Propylene Oxide | 71.7 | 0.7 |
| Propionaldehyde | 21.8 | 13.8 |
| Acetone | 6.5 | 4.3 |
| Allyl Alcohol | 0.0 | 81.0 |

As can be seen from the above results, a high yield of propylene oxide is obtained by following the teachings of the invention. Based on theoretical yield, 95% of the acetic acid is recovered. On the other hand, Run N0. B results in the formation of essentially no propylene oxide. This confirms the finding of U.S. Pat. No. 2,415,378 wherein pyrolysis of propylene hydroxyacetate yielded no propylene oxide. In Run No. A, an additional 3.5% of the hydroxyacetate of propylene is disproportionated to equimolar amounts of propylene diacetate and propylene glycol.

EXAMPLE 2

Using the apparatus described in Example 1, Run A is repeated, using potassium borate ($K_2B_4O_7$) as the basic material. A 50—50 mixture of m-xylene solvent and propylene hydroxyacetate is fed at a rate of 50 ml./hour to the tubular reactor maintained at 405° C. The conversion is 17.7% and the selectivities are as shown below:

|  | Percent |
|---|---|
| Propylene Oxide | 68.2 |
| Propionaldehyde | 20.6 |
| Acetone | 11.2 |

An additional 2.3% of the hydroxyacetate disproportionated. Based on theoretical yield, 89% of the acetic acid is recovered.

EXAMPLE 3

The apparatus in Example 1 is filled with sodium pyrophosphate ($Na_4P_2O_7$) in place of the $Na_2B_4O_7$. A 50—50 weight mixture of m-xylene and the propylene hydroxyacetate is fed at a rate of 60 ml./hour. At 430° C., the conversion is 36.2%. The selectivities are as given below:

|  | Percent |
|---|---|
| Propylene Oxide | 34.7 |
| Propionaldehyde | 20.1 |
| Acetone | 4.2 |
| Allyl Alcohol | 41.0 |

An additional 13.8% is disproportionated and 92% of the theoretical yield of acetic acid is recovered.

EXAMPLE 4

The apparatus in Example 1 is used but packed with $CaB_4O_7$, instead of the $Na_2B_4O_7$. The 50—50 mixture of m-xylene and the propylene hydroxyacetate is fed at 60 ml./hour at 370° C. The conversion is 11.4% and the molar selectivities are as shown below:

|  | Percent |
|---|---|
| Propylene Oxide | 48.9 |
| Propionaldehyde | 40.5 |
| Acetone | 10.6 |

An additional 3.6% to disproportionated products are formed and 87% of the theoretical yield of acetic acid is recovered.

EXAMPLE 5

The reaction system is Example 1 is now filled with BaO and the 50—50 weight mixture of m-xylene and propylene hydroxyacetate is fed at 60 ml./hour. At an average reactor temperature of 350° C., the conversion is 10.8% and the molar selectivities are as shown below:

|  | Percent |
|---|---|
| Propylene Oxide | 68.0 |
| Propionaldehyde | 25.6 |
| Acetone | 6.4 |

An additional 3.2% to the disproportionation products are formed and over 80% of the theoretical yield of acetic acid is recovered.

EXAMPLE 6

In the apparatus described in Example 1, Run A, a mixture of 75% by weight of m-xylene and 25% of ethylene hydroxyacetate is fed at a rate of 60 ml./hour and a temperature of 360° C. over the $Na_2B_4O_7$. The results of this experiment are summarized below:

|  | Percent |
|---|---|
| Conversion | 25 |
| Selectivity to: |  |
| Ethylene Oxide | 52 |
| Acetaldehyde | 48 |

In addition to these light products, around 25% of the converted feedstock is disproportionated to ethylene glycol and ethylene diacetate. Based on theoretical yield, 95% of the acetic acid is recovered.

EXAMPLE 7

In the apparatus and with the amount of sodium borate and conditions described in Example 1, Run No. A, the hydroxyacetate of 2-butene is used as the reactant. Butylene oxide and acetic acid are produced.

EXAMPLE 8

Using the apparatus, the amount of sodium borate and the flow rate described in Example 1, Run No. A is repeated, except that the hydroxypropionate of propylene is used as the reactant at a temperature of 375° C. The product analysis for this example is given below:

|  | Percent |
|---|---|
| Conversion | 21 |
| Selectivity to: |  |
| Propylene Oxide | 73 |
| Propionaldehyde | 20 |
| Acetone | 7 |
| Allyl Alcohol | 0 |

Some of the hydroxypropionate of propylene is disproportionated as indicated by trace amounts of propylene glycol and propylene dipropionate. About 95% of the theoretical amount of propionic acid formed is recovered.

EXAMPLE 9

Using the apparatus described in Example 1, 13.6 grams of 8–12 mesh sodium carbonate are packed in the 13 inch long tube. A mixture of 50% propylene monoacetate and 50% m-xylene is fed at a rate of 60 ml./hour at a temperature of 270° C. The results are:

|  | Percent |
|---|---|
| Conversion | 7 |
| Selectivity to: |  |
| Propylene Oxide | 85 |
| Propionaldehyde | 15 |

Approximately 50% of the reacted monoacetate is converted to an equimolar mixture of propylene glycol and propylene diacetate. The acetic acid recovery is essentially nothing. When the oven temperature is raised to 330° C., the reactor plugs. The solid material is found to be a mixture of sodium carbonate and sodium acetate.

EXAMPLE 10

In the apparatus described in Example 1, 16.8 grams of $CaCO_3$ are used as the basic material. A 50—50 mixture of propylene hydroxyacetate and m-xylene at a flow rate of 60 ml./hour and a temperature of 380° C. is reacted. The results are:

|  | Percent |
|---|---|
| Conversion | 6 |
| Selectivity to: |  |
| Propylene Oxide | 52 |
| Propionaldehyde | 38 |
| Acetone | 10 |

No detectable amounts of propylene glycol and propylene acetate are found. At 440° C., the reactor plugs. Chemical analysis shows that calcium acetate is present in the solid. Only 48% of the theoretical yield of acetic acid is recovered.

EXAMPLE 11

The apparatus of Example 1 is charged with 10% potassium acetate (20.27 grams) on alundum (8–12 mesh). A 52:48 weight mixture of benzene and propylene hydroxyacetate is fed at the rate of 4.11 grams per minute. At 396° C. and 1 atmosphere pressure, the conversion is 18.7%. The selectivities are as given below:

|  | Percent |
|---|---|
| Propylene Oxide | 76.4 |
| Propionaldehyde | 16.7 |
| Acetone | 6.9 |

An additional 4.3% is disproportionated and 93% of the theoretical yield of acetic acid is recovered.

The following two examples show the increased conversion obtained by using reduced pressure operation:

EXAMPLE 12

The process described in Example 11 is repeated except that the reaction pressure is 360 mm Hg (0.47 atmospheres) and the feed rate of the reactant is 2.47 grams of 100% propylene hydroxyacetate per minute. Conversion of hydroxyacetate is 19.9% and the selectivities are as given below:

|  | Percent |
| --- | --- |
| Propylene Oxide | 79.1 |
| Propionaldehyde | 14.5 |
| Acetone | 6.4 |

An additional 3.5% is disproportionated and 97% of the acetic acid is recovered.

EXAMPLE 13

The process described in Example 11 is repeated except that the reaction pressure is 180 mm Hg (0.24 atm.) and the feed rate is 0.74 grams per minute. Conversion of hydroxyacetate is 31.0% and the selectivities are as given below:

|  | Percent |
| --- | --- |
| Propylene Oxide | 76.8 |
| Propionaldehyde | 15.0 |
| Acetone | 8.2 |

An additional 3.2% is disproportionated and 92% of the theoretical yield of acetic acid is recovered.

EXAMPLE 14

A Hoke bomb fitted with a ¼ inch stainless steel inlet tube is charged with 14.7 grams of sodium acetate. The tube is heated to about 325° C. at which temperature the sodium acetate is molten. Passage of hydroxypropylacetate through the molten catalyst system produced propylene oxide in 80.2% selectivity at 17.3% conversion.

EXAMPLE 15

This example illustrates a preferred two-step process for producing oxiranes from olefins.

Propylene and oxygen are passed through a solution in a one gallon stirred autoclave at a temperature of 65° C. at a total pressure of five atmospheres. The solution consists of 1050 grams of acetic acid containing 9 grams of palladous chloride and 42 grams of lithium nitrate. A total of 54.5 grams of propylene and 19.6 grams of oxygen are passed through the solution. After a reaction period of 3.5 hours, the autoclave is depressured and the contents filtered. As analysed by gas chromatography it is determined that 72% of the propylene is converted with a selectivity of 74% to the vicinal isomers of the hydroxyacetates of propylene. The filtrate is subjected to vacuum distillation and the unreacted acetic acid removed overhead and recycled to the autoclave. The bottoms are admixed with water and heptane. Catalyst is dissolved in the water phase and recovered for reuse and the hydroxyacetates dissolved in the heptane phase.

After separation of the heptane, the isomeric mixture, in accordance with the procedures described in Example 1, is reacted in the presence of sodium borate at a temperature of 385° C. Of the material converted, 35 mole % each of propylene oxide and acetic acid are obtained. The acetic acid co-product is recycled to the first reaction zone and further reacted with propylene to make additional amounts of the hydroxyacetates of propylene. Hence, it can be seen that the acetic acid may be fully recycled. In practice, a small amount of the acetic acid may be purged from the system to avoid the build-up of unwanted impurities.

EXAMPLE 16

The process described in Example 1 is repeated except that the basic reactant is 7.51 grams of sodium aluminate (12.8% on alundum) and the reaction temperature is 400° C. The conversion of the hydroxyacetate is 25.7%. and the selectivities to propylene oxide, propionaldehyde and acetone are 68.4%, 22.4% and 9.2%, respectively.

EXAMPLE 17

The procedure of Example 15 is repeated with the exception that 7.39 grams of sodium silicate (14,3% on alundum) is used as the basic reactant. Conversion of the hydroxyacetate is 27.1% and selectivities to propylene oxide, propionaldehyde and acetone are 70.4%, 22.3% and 7.3%, respectively.

COMPARATIVE EXAMPLE A

The apparatus in Example 1 is filled with activated alumina which, under the reaction conditions, contains acid sites. Again a 50—50 mixture of m-xylene and propylene hydroxyacetate is fed to the reactor at a rate of 60 ml./hour. The conversion, when the average temperature is 265° C., is 29%. The selectivity to various products is tabulated below:

|  | Mole Percent |
| --- | --- |
| Propylene Oxide | 0.0 |
| Propionaldehyde | 76.5 |
| Acetone | 11.8 |
| Allyl Alcohol | 11.8 |

An additional 11% is converted to disporportionation products.

COMPARATIVE EXAMPLE B

Fifty ml. of a 10% NaOH solution are mixed with 14.8 grams of propylene hydroxyacetate at room temperature. The temperature increases up to 50° C. After 35 minutes, a sample is taken and the liquid analyzed. This shows that the main product is propylene glycol. No detectable amounts of propylene oxide or acetic acid are measured. The propylene hydroxyacetate is completely converted in the short reaction time. This example clearly shows that the procedure shown in U.S. Pat. No. 3,453,189 is not a viable method for the preparation of oxiranes.

Having thus described our invention, what we claim and desire to protect by Letters Patent is:

1. In a process for the preparation of oxirane compounds which comprises the deacyloxylation of vicinal hydroxyesters derived from oxygen, an olefin, and a carboxylic acid, wherein the olefin is ethylene, propylene, a butylene, a pentene, styrene, or alphamethylstyrene, and the carboxylic acid is acetic, propionic, or butyric, the improvement which comprises performing said deacyloxylation reaction in the vapor phase at a temperature of from 250 to 600° C in the presence of a basic material having a pH of from 8 to 13 in a 0.1 molar aqueous solution.

2. The process of claim 1 wherein the basic material is an alkaline carboxylate.

3. The process of claim 1 wherein the basic material is sodium silicate or sodium aluminate.

4. The process of claim 1 wherein the deacyloxylation is carried out at a partial pressure of from 1 to 15 psi of the hydroxyester compound.

5. A process for the preparation of oxiranes which comprises reacting an olefin with oxygen and a carboxylic acid to form a vicinal hydroxyester, wherein the olefin is ethylene, propylene, a butylene, a pentene, styrene, or alpha-methylstyrene, and the carboxylic acid is acetic, propionic, or butyric; deacyloxylating said hydroxyester in the vapor phase at a temperature of from 250° to 600° C in the presence of a basic material having a pH of from 8 to 13 in a 0.1 molar aqueous solution, thereby forming said oxirane and a carboxylic acid; and recycling the carboxylic acid thus formed to the first reaction step.

6. The process of claim 5 wherein said carboxylic acid is acetic acid.

7. The process of claim 5 wherein said basic material is an alkaline carboxylate.

8. In a process for the preparation of oxirane compounds which comprises the deacyloxylation of vicinal hydroxyester compounds derived from oxygen, an olefin, and a carboxylic acid, wherein the olefin is ethylene, propylene, a butylene, a pentene, styrene, or alphamethylstyrene, and the carboxylic acid is acetic, propionic, or butyric, the improvement which comprises performing said deacyloxylation reaction in the vapor phase at a temperature of from 250° to 600° C in the presence of a basic material, said basic material being an alkali or alkaline earth metal of a borate, phosphate, oxide, or carbonate.

9. The process of claim 8 wherein the basic material is a compound of sodium, potassium, lithium, calcium, or barium.

10. A process for the preparation of oxiranes which comprises reacting an olefin with oxygen and a carboxylic acid to form a vicinal hydroxyester, wherein the olefin is ethylene, propylene, a butylene, a pentene, styrene, or alpha-methylstyrene, and the carboxylic acid is acetic, propionic, or butyric; deacyloxylating said hydroxyester in the vapor phase at a temperature of from 250° to 600° C in the presence of a basic material, said basic material being an alkali or alkaline earth metal of a borate, phosphate, oxide, or carbonate, thereby forming said oxirane and a carboxylic acid; and recycling the carboxylic acid thus formed to the first reaction step.

11. The process of claim 10 wherein the basic material is a compound of sodium, potassium, lithium, calcium, or barium.

12. In a process for the preparation of oxirane compounds which comprises the deacyloxylation of vicinal hydroxyester compounds derived from oxygen, an olefin, a carboxylic acid, wherein the olefin is ethylene, propylene, a butylene, a pentene, styrene, or alphamethylstyrene, and the carboxylic acid is acetic, propionic, or butyric, the improvement which comprises performing said deacyloxylation reaction in the vapor phase at a temperature of from 250° to 600° C in the presence of an alkaline carboxylate, wherein the carboxylate corresponds to the carboxylic acid co-product.

13. The process of claim 12 wherein the alkaline carboxylate is formed in situ.

14. The process of claim 12 wherein the olefin is ethylene and the carboxylic acid is acetic.

15. The process of claim 12 wherein the olefin is propylene and the carboxylic acid is acetic.

16. The process of claim 12 wherein the olefin is a butylene and the carboxylic acid is acetic.

* * * * *